(12) United States Patent
Shin et al.

(10) Patent No.: US 9,681,953 B2
(45) Date of Patent: Jun. 20, 2017

(54) COMPLEX SUPPORT BODY FOR REGENERATING BONE-CARTILAGE, METHOD FOR MANUFACTURING THEREOF, AND COMPOSITION FOR TREATING BONE AND CARTILAGE RELATED DISEASES COMPRISING SAME AS ACTIVE INGREDIENT

(75) Inventors: Jung Woog Shin, Busan (KR); Ji Won Shin, Changwon-si (KR); So Hee Park, Ulsan (KR)

(73) Assignee: INJE UNIVERSITY INDUSTRY-ACADEMIC COOPERATION FOUNDATION, Gimhae-si, Gyeongsangnam-Do (KR)

( * ) Notice: Subject to any disclaimer, the term of this patent is extended or adjusted under 35 U.S.C. 154(b) by 73 days.

(21) Appl. No.: 14/006,401

(22) PCT Filed: Feb. 20, 2012

(86) PCT No.: PCT/KR2012/001270
§ 371 (c)(1),
(2), (4) Date: Sep. 20, 2013

(87) PCT Pub. No.: WO2012/134059
PCT Pub. Date: Oct. 4, 2012

(65) Prior Publication Data
US 2014/0012393 A1    Jan. 9, 2014

(30) Foreign Application Priority Data
Mar. 31, 2011    (KR) .................. 10-2011-0029815

(51) Int. Cl.
*A61F 2/28*    (2006.01)
*A61L 27/12*    (2006.01)
(Continued)

(52) U.S. Cl.
CPC ............ *A61F 2/28* (2013.01); *A61F 2/30756* (2013.01); *A61L 27/12* (2013.01); *A61L 27/3817* (2013.01);
(Continued)

(58) Field of Classification Search
None
See application file for complete search history.

(56) References Cited

U.S. PATENT DOCUMENTS

| 6,626,950 B2 * | 9/2003 | Brown et al. .............. 623/23.72 |
| 2005/0112397 A1 * | 5/2005 | Rolfe ................. A61B 17/8605 428/593 |

(Continued)

FOREIGN PATENT DOCUMENTS

| CN | 101574540 A | * 11/2009 |
| KR | 10-2008-0113013 A | 12/2008 |

(Continued)

OTHER PUBLICATIONS

English translation for CN101574540.*
(Continued)

*Primary Examiner* — David H Willse
*Assistant Examiner* — Javier Blanco
(74) *Attorney, Agent, or Firm* — Lucas & Mercanti, LLP

(57) ABSTRACT

The present invention relates to a complex support body for regenerating bone-cartilage, a method for manufacturing thereof, and a composition for treating bone and cartilage related diseases comprising the same as an active ingredient, and more particularly, to a complex support body for regenerating bone-cartilage, which comprises a bone regeneration layer consisting of a biodegradable polymer and a biocompatible ceramic, and a cartilage regeneration layer, which is coupled to the bone regeneration layer and in which cells that can be differentiated into cartilages cells are fixed; a (Continued)

method for manufacturing thereof; and a composition for treating bone and cartilage related diseases comprising the same as an active ingredient. The complex support body of the present invention for regenerating bone-cartilage is manufactured as a three-dimensional support body, which is similar to a living tissue, according to a bioplotting method, and exerts the effect of regeneration into a bone tissue and a cartilage tissue, respectively, depending on materials encountered in the environment where the complex support body for regenerating bone-cartilage is used.

2 Claims, 3 Drawing Sheets

(51) Int. Cl.
    *A61L 27/56* (2006.01)
    *A61L 27/38* (2006.01)
    *A61L 27/54* (2006.01)
    *A61L 27/58* (2006.01)
    *A61F 2/30* (2006.01)
(52) U.S. Cl.
    CPC ............... *A61L 27/54* (2013.01); *A61L 27/56* (2013.01); *A61L 27/58* (2013.01); *A61F 2/3094* (2013.01); *A61F 2002/30766* (2013.01); *A61L 2430/02* (2013.01); *A61L 2430/06* (2013.01)

(56) References Cited

U.S. PATENT DOCUMENTS

| | | | |
|---|---|---|---|
| 2006/0141012 A1* | 6/2006 | Gingras | A61F 2/08 424/442 |
| 2007/0112397 A1* | 5/2007 | Crivelli | H04L 27/2003 607/60 |
| 2009/0012629 A1* | 1/2009 | Yao | A61F 2/30756 623/23.72 |
| 2009/0232875 A1* | 9/2009 | Tampieri et al. | 424/444 |

FOREIGN PATENT DOCUMENTS

| KR | 10-2009-0010607 A | 1/2009 |
|---|---|---|
| KR | 10-2010-0104219 A | 9/2010 |
| KR | 10-2011-0025327 A | 3/2011 |

OTHER PUBLICATIONS

International Search Report of PCT/KR2012/001270 dated Oct. 25, 2012.
JoonGon Son et al; Fabrication of Tailor-Made 3D PCL Scaffold Using a Bio-Plotting Process; Polymer (Korea) 2008; vol. 32, No. 2; pp. 163-168.

\* cited by examiner

COMPLEX SUPPORT BODY FOR REGENERATING BONE-CARTILAGE, METHOD FOR MANUFACTURING THEREOF, AND COMPOSITION FOR TREATING BONE AND CARTILAGE RELATED DISEASES COMPRISING SAME AS ACTIVE INGREDIENT

CROSS-REFERENCE TO RELATED APPLICATIONS

This application is a 371 of PCT/KR2012/001270 filed on Feb. 20, 2012, which claims the priority of Korean Patent Application Serial No. 10-2011-0029815 filed on Mar. 31, 2011, the contents of each of which are incorporated herein by reference.

FIELD OF THE INVENTION

The present invention relates to a complex support body for regenerating bone-cartilage, a method for manufacturing the complex support body, and a composition for treating the damaged bones and cartilages comprising the complex support body for regenerating bone-cartilage as an active ingredient.

BACKGROUND OF THE INVENTION

Tissue engineering is one of new fields emerged with the development of science. It is a multidisciplinary science integrating basic concept such as life science, engineering and medicine with scientific technologies for understanding correlation between structure and functions of biological tissues, and further an applied science objected to maintain, enhance or recover functions of the body by making artificial tissues, which can be transplanted to the body for replacing or regenerating damaged tissues or organs to normal tissue.

A representative tissue engineering technique applies a technique comprising the following procedures. First of all, a required tissue is collected form a patient body, cells are isolated form the tissue sample, the isolated cells are proliferated as needed by culture, the proliferated cells are seeded to a porous biodegradable polymer support body and cultured in vitro for a certain period of time to obtain a hybrid type cell/polymer structure, and then the structure is transplanted to the human body again. In the case of most tissues or organs, the cells after transplantation are supplied with oxygen and nutrients by body fluid diffusion until new blood vessels are formed, and then when blood is supplied through blood vessels grown in the human body, cells are proliferated and differentiated so as to form new tissues and organs, while the polymer support body is removed by degradation.

Thus, for this tissue engineering study, first of all, it is important to manufacture a biodegradable polymer support body, which is similar with a living tissue. Main requirements of support body materials used for regenerating human tissues are that: it should play a role as a substrate or a frame so as to make tissue cells adhere to the material surface and to form a tissue having a three dimensional structure, and it should also play a role as a middle barrier located between the transplanted cells and host cells. This means that it should have non-toxic biocompatibility not causing blood clotting or inflammatory reaction after transplantation.

When a joint is damaged, the damaged joint is difficult to be autochthonously regenerated because there is no blood vessels, nerves and lymphatic tissues in the articular cartilage. Accordingly, in the articular cartilage, small damage may cause development of wound and degeneration of the joint. Thus, in order to recover and maintain functions of bone and cartilage tissues, many medical methods are being attempted.

A cartilage is a tissue embryologically derived from the mesoderm like as a bone tissue, and forms an endoskeleton together with a bone. Further, when the cartilage is severely damaged, a bone tissue below the cartilage as well as the cartilage may be damaged. Like this, the cartilage and the bone are intimately working tissues, but the previous tissue engineering therapy of the bone and the cartilage treated them separately.

Specifically, as previous operation methods for clinically regenerating cartilages, method for regenerating only cartilages, for example: (1) a method of inducing differentiation of stem cells into cartilage cells, (2) a method of transplanting bone tissues, cartilage tissues, self or homogeneous cartilage tissues to the cartilage defected region, (3) a method of transplanting tissues (perichondrium or periosteum) or compounds, which can induce cartilages, on the surface, of the cartilage defected region, and (4) a method of inducing cartilage regeneration by transplanting cartilage cells to the cartilage defected region by cartilage cell implantation are used.

However, as mentioned above, the bone and the cartilage are intimately working tissues. Accordingly, in the case of the previous method treating the cartilage and the bone separately, there were problems of weak cohesiveness and long recovering time.

In order to solve the problems, support bodies, which can treat the bone and the cartilage at the same time, are being developed.

For tissue engineering articular cartilage regeneration, C. Hassper et al manufactured an osteochondral construct by modeling an articular surface through CT image and by machining the surface identically with a real articular surface. (Carl Haasper, et. al, "A system for engineering an osteochondral construct in the shape of an articular surface: Preliminary results," Annals of Anatomy, Vol. 190, pp. 351~359 2008). They manufactured the construct as a dual structure by compressing collagen-1, where cells are planted on one side thereof, by using a commercialized Tutobone (heterogeneous bone graft). However, there were problems that the materials are very expensive, and it is impossible to control the internal structure of a carrier. Further, in the recent studies, a complex support body manufactured by culturing each cell on a poly(glycolic acid) (PGA) support body and a poly(lactic-co-glycolic acid)/poly(ethylene glycol) (PLGA/PEG) support body of the bone part, separately followed by linking the two support bodies by using a suture (Schaefer et al., Biomaterials, 2000, 21, 2599-2606), a collagen/PLGA sponge support body (Guoping Chen et al., Materials Science and engineering C 26 (2006) 118. 123), and the like had been tried. However, development of a complex support body for bones and cartilages having excellent effect are still needed.

Further, many researchers are trying various methods for making a polymer to a porous structure, for example, a salt leaching method, which is mixing single crystal salt, drying and then leaching the salt by dissolving in water (Solvent-casting and particulate-leaching technique: A. G. Mikos et al, Polymer, 35, 1068, 1994), a method of swelling a polymer by using $CO_2$ gas (Gas foaming technique: L. D.

Harris et al, J. Biomed. Mater. Res., 42, 396, 1998), a method for making a polymer fiber to a non-woven fabric in the form of a polymer mesh (Fiber extrusion and fabric forming process: K. T. Paige et al, Tissue Engineering, 1, 97, 1995), a phase separation method making pores by soaking the solvent contained in a polymer solution in a non-solvent (Thermally induced phase separation technique: C. Schugens et al, J. Biomed. Mater. Res., 30, 449, 1996), an emulsion freeze-drying method, which is manufacturing an emulsion solution by mixing a polymer solution and water, and then freezing with liquid nitrogen so as to freeze-dry (Emulsion freeze-drying method: K. Whang et al, Polymer, 36, 837, 1995).

However, the above methods had problems that it is generally difficult to control the pore size of a support body, the surface and porosity of the obtained polymer support body, and it is difficult to form open structure between pores.

SUMMARY OF THE INVENTION

In order to solve the above-described problems associated with prior art, the present invention is objected to provide a complex support body for regenerating bone-cartilage, which can regenerate cartilage and bone tissues at the same time, and a method for manufacturing the complex support body for regenerating bone-cartilage, which controls the pore size easily, thereby manufacturing a desired three-dimensional structure.

Further, the present invention is objected to provide a composition for treating bone and cartilage related diseases comprising the complex support body for regenerating bone-cartilage as an active ingredient.

In order to accomplish one object of the present invention, the present invention provides a complex support body for regenerating bone-cartilage comprising: (a) a bone regeneration layer; and (b) a cartilage regeneration layer, which is coupled to the bone regeneration layer and in which cells that can be differentiated into cartilage cells are fixed.

The present invention further provides a composition for treating bone and cartilage related diseases comprising the complex support body for regenerating bone-cartilage of the present invention as an active ingredient.

The present invention further provides a method for manufacturing the complex support body for regenerating bone-cartilage comprising: i) a step of manufacturing a cartilage regeneration layer; ii) a step of manufacturing a bone regeneration layer; and iii) a step of linking the cartilage regeneration layer and the bone regeneration layer.

Hereinafter, the complex support body for regenerating bone-cartilage of the present invention will be described in detail.

The present invention relates to a hybrid-type complex support body for regenerating bone-cartilage, in which a bone regeneration layer and a cartilage regeneration layer are manufactured separately with different materials and then coupled to each other.

In the complex support body for regenerating bone-cartilage of the present invention, the bone regeneration layer is characterized by comprising a biodegradable polymer and a biocompatible ceramic.

The bone regeneration layer should play a role as a substrate or a frame so as to form tissues having a three-dimensional structure by adhering tissue cells on the material surface, and should also play a role as a middle barrier located between transplanted cells and host cells. Further, it should have non-toxic biocompatibility not causing blood clotting or inflammatory reaction after transplantation, and should have biodegradability, which is completely-degraded in the body a certain time after transplanted cells fully play a role as a tissue.

The biodegradable polymer may be any biopolymer known in the art if it has biodegradability. Preferably, it may be at least one biodegradable polymer selected from the group consisting of alginate, hyaluronic acid, collagen, gelatin, cellulose methyl cellulose, chitosan, poly(lactic acid), poly(glycolic acid) (PGA), poly(lactic-co-glycolic acid) (PLGA), poly-caprolactone, poly(anhydrides), poly-orthoesters, polyvinylalcohol, poly (ethylene-glycol), poly-urethane, polyacrylic acid, poly (N-isopropyl acrylamide), polyethylene oxide)-poly(propylene oxide)-poly(ethylene oxide) copolymer and a copolymer of two or more of them, and most preferably, it may be poly(lactic acid) or poly-caprolactone.

Up to now, only PGA, PLA, PLGA and the like are approved as a biodegradable polymer, which can be used to the human body, from Food and Drug Administration (FDA), and are used as a polymer support body material for in vivo regeneration of the human body tissues. The poly-(caprolactone) has low melting point and is easy for mechanical forming. And therefore, it is broadly developed and used because it can form proper mechanical strength more than a certain level; it is degraded by hydrolysis and enzyme action in the body and then released in the form of carbon dioxide and water due to its biocompatibility; and has no toxicity.

Further, in the present invention, a biocompatible ceramic is added to give enough mechanical strength to endure load in the body until tissues are regenerated to the bone regeneration layer. The biocompatible ceramic may any biocompatible ceramic known in the art, preferably, it may be at least one selected from the group consisting of hydroxyapatite (HA), ceramic-containing inorganic substances, fluorinated apatite, monocalcium calcium phosphate $Ca(H_2PO_4)_2$, dibasic calcium phosphate $(CaHPO_4)$, tribasic calcium Phosphate $(Ca_3(PO_4)_2)$, Octacalcium phosphate $Ca_8H_2(PO_4)_6 \cdot 5H_2O$, and most preferably, it may be hydroxyapatite.

In the present invention, the bone regeneration layer may comprise the biodegradable polymer in an amount of 85 to 95 wt % and the biocompatible ceramic in an amount of 5 to 15 wt %. When the amount of the biocompatible ceramic is less than 5 wt %, it may be difficult to display the desired mechanical strength, and when it is over 15 wt %, flexibility and workability may be deteriorated.

The present invention may further comprise a step of seeding cells that can be differentiated into bone cells after the bone regeneration layer is manufactured. In the case of the bone regeneration layer, it contains the biocompatible ceramic in a certain portion, and the biocompatible ceramic is melted at high temperature. Accordingly, it is preferred to manufacture the bone regeneration layer in advance, and then to seed the cells that can be differentiated into bone cells. The cells that can be differentiated into bone cells may be at least one cells selected from the group consisting of: mesenchymal stem cells and interstitial cells, which are isolated from any one of bone marrow, muscle, fat, umbilical cord, amnion and amniotic fluid; and precursor cells, which are derived from the cells and can be differentiated into bone cells.

Further, when seeding the cells that can be differentiated into bone cells, a bone morphogenic inducing factor may be further added to the support body for regenerating bones for inducing effective growth to bone cells. The bone morphogenic inducing factor may be used for coating the surface of the bone regeneration layer before seeding stem cells to the bone regeneration layer, and therefore, there may be an effect that the bone morphogenic inducing factor may be slowly released in the entire regeneration layer.

In the complex support body for regenerating bone-cartilage of the present invention, the cartilage regeneration layer may be a cell-fixed biodegradable polymer support body. In the present invention, the biodegradable polymer for forming the cartilage regeneration layer may be any biopolymer known in the art if it has degradability, and preferably, it may be alginate, hyaluronic acid, collagen, gelatin, cellulose methyl cellulose, chitosan, poly(lactic acid), poly(glycolic acid) (PGA), poly(lactic-co-glycolic acid) (PLGA), poly-caprolactone, poly(anhydrides), poly-orthoesters, polyvinylalcohol, poly(ethyleneglycol), poly-urethane, polyacrylic acid, poly (N-isopropyl acrylamide), poly(ethylene oxide)-poly(propylene Oxide)-poly(ethylene oxide) copolymer and a copolymer of two or more of them, and most preferably, it may be alginate. The biodegradable polymer for forming the bone regeneration layer and the biodegradable polymer for forming the cartilage regeneration layer may be the same or different each other.

In the present invention, the cartilage regeneration layer is characterized that the cells that can be differentiated into cartilage cells are fixed therein.

Namely, in the present invention, in the case of the cartilage regeneration layer, the biodegradable polymer support body and the cells that can be differentiated into cartilage cells are mixed, and then a support body is manufactured by using the mixture. The biodegradable polymer for the cartilage regeneration layer may be alginate, which is generally used for differentiating mesenchymal stem cells and the like into cartilage cells, preferably.

The cells that can be differentiated into cartilages cells may be at least one cells selected from the group consisting of: mesenchymal stem cells and interstitial cells, which are isolated from any one of bone marrow, muscle, fat, umbilical cord, amnion and amniotic fluid: and precursor cells, which are derived from the cells and can be differentiated into bone cells.

In the present invention, the bone regeneration layer and the cartilage regeneration layer may comprise pores in the size of 50 to 700 μm.

In the complex support body for regenerating bone-cartilage according to the present invention, it is also possible to further seed stem cells that can be differentiated into bone cells or cartilage cells separately after coupling the bone regeneration layer and the cartilage regeneration layer. Further, it is also possible to further add a bone morphogenic inducing factor during the step of seeding the stem cells.

The complex support body for regenerating bone-cartilage according to the present invention can effectively induce bone tissues and cartilage tissues by stem cells contained during the process of manufacturing the cartilage regeneration layer itself and differentiation of the seeded stem cells after manufacturing the bone regeneration layer, and can exert excellent mechanical strength and flexibility and maintain a constant shape by because it comprises a polymer support body. Accordingly, the complex support body for regenerating bone-cartilage according to the present invention can be usefully used as a therapeutic agent, which can effective treat or regenerate damaged bone tissues and cartilage tissues, by being transplanted into the body.

Further, the present invention includes a composition for treating cartilage damage comprising the complex support body for regenerating bone-cartilage according to the present invention as an active ingredient. The composition for treating cartilage damage according to the present invention may be usefully used for restoring cartilage defect, which is generated by trauma on articular cartilage, cranium face, auricle, nose, joint and the like; congenital malformation; part for foreign matter removing; degeneration by aging; and the like. In the present invention, the composition for treating cartilage-bone related diseases may further comprise a bone morphogenic inducing factor.

Hereinafter, a method for manufacturing the complex support body for regenerating bone-cartilage of the present invention will be described in detail.

In the present invention, the complex support body for regenerating bone-cartilage is characterized that the bone regeneration layer and the cartilage regeneration layer are manufactured separately by a bioplotting technique of a rapid prototype method, and then coupled to each other.

"Rapid Prototyping Technology (RP)" is a process of new and innovative concept, which can see a product by immediately prototyping three dimensional modeling CAD data such as Rhino 3D(.stl) with materials such as plastic, wax, paper, photocurable resin and metal. The rapid prototyping method was developed around 1986 at USA for the first time, and then is being commercialized in earnest with 1988 as the peak. This method is characterized by reducing production time by integrating trial and error, which are required from product design to manufacture of a prototype and mass production of a complete product on the basis of a computer. Particularly, there is another advantage that near net shape may be formed in the ceramics field.

The bioplotting technique is one of the rapid prototype methods, and is a method plotting by extruding materials with some viscosity through a fine nozzle. When using the bioplotting technique, an environment suitable for growth of cartilage cell and bone cells can be provided by embodying a cross-linked porous structure.

In the present invention, the step of manufacturing the cartilage regeneration layer is characterized by comprising: i-1) a step of mixing alginate to a solution containing a cell culture medium, 0.3 wt % $CaCl_2$ and 0.15 M NaCl up to 4 wt % to prepare cross-linked alginate; i-2) a step of mixing cells that can be differentiated into cartilages cells to the cross-linked alginate; and i-3) a step of manufacturing the cartilage regeneration layer by using the mixture of the cross-linked alginate and the cells that can be differentiated into cartilages cells according to a rapid prototype method.

The cell culture medium may be any cell culture medium known to those skilled in the art, and preferably, it may be a medium, in which 0.3 wt % calcium chloride and 0.15 mol sodium chloride are mixed to Dulbecco's Modified Eagle's Medium-High glucose (DMEM-HG, Gibco) supplemented with 1 vol % penicillin/streptomycin solution. Alginate is mixed to the above medium up to 4 wt % by using a vortex mixer for 30 min, thereby manufacturing a cross-linked alginate, and then transfer to a syringe for plotting.

In the i-2) step, the cells that can be differentiated into cartilage cells are mixed to the cross-linked alginate to the range of $10^5$ to $10^{10}$ cells/ml.

When manufacturing the cartilage regeneration layer, a Whatman qualitative filter paper (Z240079 Sigma-Aldrich) is spread on the floor surface where the support body will be manufacture, 5 wt % calcium chloride solution is properly sprayed on the floor surface for curing the cross-linked alginate, and then 5 wt % calcium chloride solution is sprayed several times while manufacturing the support body.

When manufacturing the cartilage regeneration layer, a bone morphogenic inducing factor may be further added. The bone morphogenic inducing factor may comprise various factors known in the art, and helps to differentiation and growth of stem cells into cartilage cells and bone cells. When manufacturing the support body for regenerating cartilages, if the bone morphogenic inducing factor is added to alginate, the bone morphogenic inducing factor is slowly released as the alginate is absorbed in the human body. Accordingly, it is preferred because the bone morphogenic inducing factor has sustained release.

Specifically, the bone morphogenic inducing factor is preferred to be at least one selected from the group consisting of bone morphogenic protein (BMP), Transforming growth factor (TGF-β: transforming growth factor β), osteoinductive factor (OIF), insulin-like derived growth factor (IGF), platelet derived growth factor (PDGF) and fibroblast growth factor (FGF). Preferably, in the present invention, the bone morphogenic inducing factor used for applying the member for regenerating bone-cartilage to the human body may be recombinant human bone morphogenic factor (rhBMP).

In the present invention, the step of manufacturing the bone regeneration layer is characterized by comprising:

a step of manufacturing the bone regeneration layer comprising ii-1) a step of dissolving a biodegradable polymer by heating; ii-2) a step of mixing the biodegradable polymer of 85 to 95 wt % and a biocompatible ceramic of 5 to 15 wt % followed by stirring and cooling thereof for solidification; and II-3) a step of manufacturing a support body by using the solidified material according to a rapid prototype, bioplotting method; and ii-4) a step of seeding cells that can be differentiated into bone cells to the manufactured bone regeneration layer.

The cells that can be differentiated into bone cells may be at least one cells selected from the group consisting of: mesenchymal stem cells and interstitial cells, which are isolated from any one of bone marrow, muscle, fat, umbilical cord, amnion and amniotic fluid; and precursor cells, which are derived from the cells and can be differentiated into bone cells, preferably.

In the present invention, the rapid prototype method comprises various methods known to those skilled in the art, and the entire size of the bone regeneration layer, pore size, thickness of a strand forming the regeneration layer, and the like may be properly selected depending on the shape and characteristics of the region, where the complex support body for regenerating bone-cartilage of the present invention is to be applied.

In the present invention, in the step of linking the cartilage regeneration layer and the bone regeneration layer, it is characterized that the manufactured cartilage regeneration layer and bone regeneration layer are linked by at least one glue selected from the group consisting of fibrin glue, gelatin glue, polyurethane-containing glue and cyanoacrylate-containing glue.

General methods for linking the cartilage regeneration layer and the bone regeneration layer may be a method of lyophilizing by using a cross-linker or a method of linking by using a biocompatible glue, and in the present invention, the method using a glue is used.

As the biocompatible glue, there are fibrin glue, gelatin glue, polyurethane-containing glue and cyanoacrylate-containing glue. Herein, the polyurethane-containing glue or the cyanoacrylate-containing glue may be difficult to be controlled due to their toxicity, and thus, it is preferred to be linked with the fibrin glue and the gelatin glue.

In the method of linking the bone regeneration layer and the cartilage regeneration layer with the fibrin glue, first of all, fibrinogen solution and thrombin solution are prepared, and the fibrinogen solution 0.15 ml is coated on the support body for regenerating cartilages, and then immediately, the thrombin solution is coated thereon to link the support body for regenerating bones.

In the present invention, it is also possible to further seed the bone morphogenic inducing factor and the stem cells that can be differentiated into bone cells or cartilage cells in the future to the complex support body, after linking the bone regeneration layer and the cartilage regeneration layer.

Advantageous Effects of the Invention

The present Invention is about a complex support body for regenerating bone-cartilage. It has effects that it is possible to regenerate bones and cartilages in a complex by solving the problem of linking of cartilages to bone tissues, and it provides a complex support body, which can be differentiated into bone cells in a support body for regenerating bones and into cartilage cells in a support body for regenerating cartilages by stem cell differentiation.

BRIEF DESCRIPTION OF THE DRAWINGS

The above and other objects and features of the present invention will become apparent from the following description of the invention taken in conjunction with the following accompanying drawings, which respectively show.

DETAILED DESCRIPTION OF THE INVENTION

Figure 1:
FIG. 1: an image of a bone regeneration layer manufactured by a rapid prototype method of Example 1.
Figure 2:
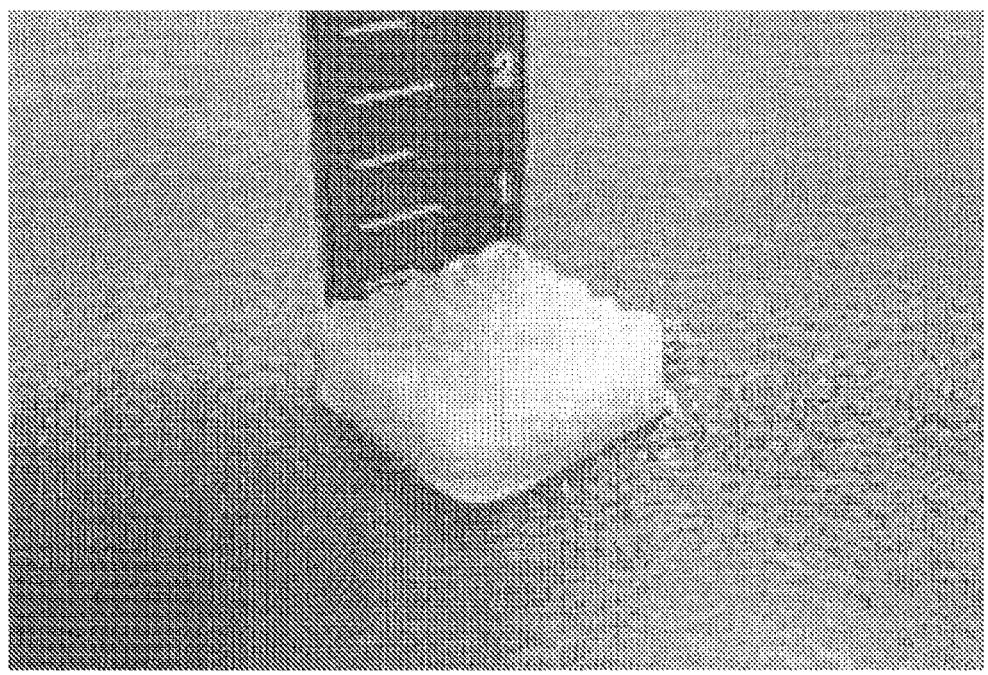
FIG. 2: an image of a cartilage regeneration layer manufactured by a rapid prototype method of Example 2.
Figure 3:
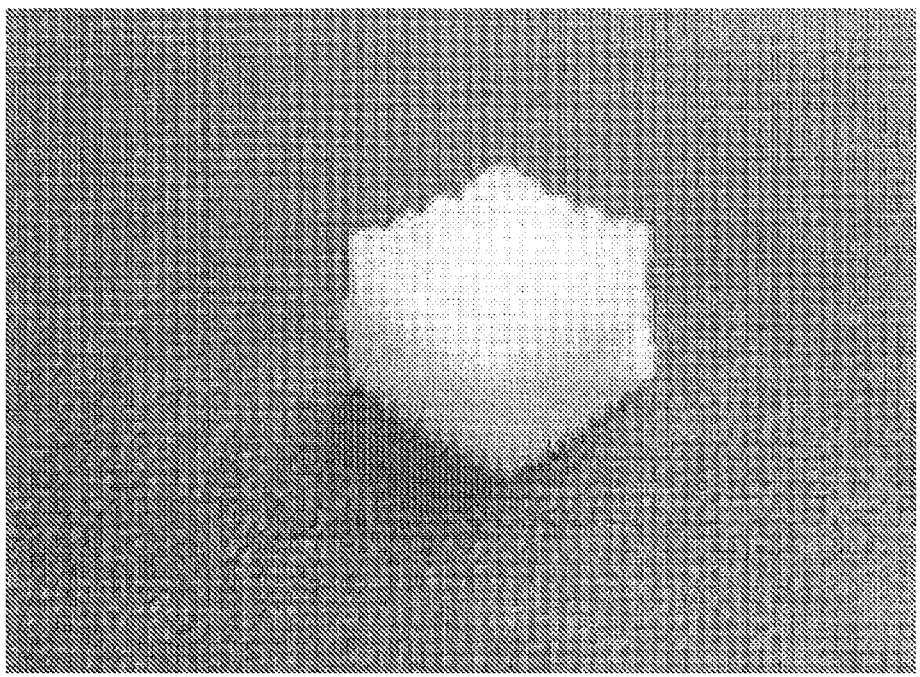
FIG. 3: an image of a complex support body for regenerating bone-cartilage, in which a bone regeneration layer and a cartilage regeneration layer are coupled, of Example 3.

Hereinafter, the present invention is explained by the following Examples and Test Examples in more detail. The following Examples and Test Examples are intended to further illustrate the present invention, and the scope of the present invention cannot be limited thereby in any way.

Example 1: Manufacture of Bone Regeneration Layer

First of all, poly-caprolactone (PCL, Polyscience, Inc., MW. 50,000) was dissolved by heating to 120° C., and then hydroxyapatite (HA, 289396, Sigma-Aldrich) was mixed thereto by stirring for 5 hours up to 10 wt % of the final solution.

The mixed final solution was cooled to solidify, the solid was cut into the proper size, and then transferred to a syringe for plotting.

A poly-caprolactone/hydroxyapatite (PCL/HA) support body for regenerating bones (pore size: 450 μm, width 1 cm×length 1 cm×height 0.5 cm) was manufactured with the syringe (100° C., pressure 550 kPa and 350 μm) through bioplotting system (M4T, Korea). A support body for regenerating bones was completed by seeding rabbit mesenchymal stem cells of $10^6$ cells/ml to the poly-caprolactone/hydroxyapatite (PCL/HA) support body.

Example 2: Manufacture of Cartilage Regeneration Layer

Example 2-1 Preparation of Cross-Linked Alginate 0.3 wt % calcium chloride (Junsei Chemical Co., Ltd) and 0.15 mol sodium chloride (Junsei) were mixed to Dulbecco's Modified Eagle's Medium-high glucose (DMEM-HG, Gibco) supplemented with 1 vol % penicillin (100 U/ml)/streptomycin (100 µm/ml) solution. Alginate (A0628, Sigma) obtained brown alga from was mixed to the above mixed solution by using a vortex mixer tor 30 min up to 4 wt % of the final solution mixture. The final solution was transferred to a syringe for plotting to obtain a cross-linked alginate.

Example 2-2 Preparation of Calcium Chloride Solution

For curing alginate, 5 wt % calcium chloride to distilled water, and then stirred for 2 to 3 hours followed by filtration.

Example 2-3 Manufacture of Support Body for Regenerating Cartilage

Rabbit mesenchymal stem cells were mixed to the cross-linked alginate manufactured in Example 2-1 to the concentration of $10^6$ cells/ml. The mixed solution was subjected to cell plotting with the desired bioplotting system (M4T, Korea) at the condition of temperature of 20° C. and pressure of 200 kPa by using a 350 µm syringe to manufacture an alginate support body for regenerating cartilages (width and length of 3 cm, height: 1 cm).

At this time, for keeping an aseptic condition, cell plotting was conducted in a clean bench. Further, the prepared 5 wt % calcium chloride solution was properly sprayed a petri dish, in which Whatman qualitative filter paper (Z240079, Sigma-Aldrich) was spread on the floor surface where the support body will be manufactured, and then cell plotting was conducted. The 5 wt % calcium chloride solution was sprayed several times while manufacturing the support body.

Example 3: Manufacture of Complex Support Body for Regenerating Bone-Cartilage

The PCL/HA support body for regenerating bones and the alginate support body for regenerating cartilage manufactured in Examples 1 and 2 were coupled to each other by using a fibrin glue (Greenplast Kit 1 ml, Green Cross Corp., Korea).

First of all, a fibrinogen solution and a thrombin solution were prepared, respectively. The fibrinogen solution 0.15 ml was dropped to the alginate support body, and then immediately, the thrombin solution was coated thereon to link the PCL/HA support body followed by storing at room temperature for 5 min to manufacture a complex support body for regenerating bone-cartilage.

INDUSTRIAL APPLICABILITY

The present invention is about a complex support body for regenerating bone-cartilage. It has effects that it is possible to regenerate bones and cartilages in a complex by solving the problem of linking of cartilages to bone tissues, and it provides a complex support body, which can be differentiated into bone cells in a support body for regenerating bones and into cartilage cells in a support body for regenerating cartilages by stem cell differentiation.

While the invention has been described with respect to the above specific embodiments, it should be recognized that various modifications and changes may be made and also fail within the scope of the invention as defined by the claims that follow.

What is claimed is:

1. A bone-cartilage regeneration support body for regenerating bone-cartilage, the support body comprising:
    (a) a bone regeneration layer, in which cells that can be differentiated into bones cells are fixed; and
    (b) a discrete cartilage regeneration layer, which is coupled to the bone regeneration layer and in which cells that can be differentiated into cartilage cells are fixed,
    wherein:
        the bone regeneration layer comprises a biodegradable polymer in an amount of 85 to 95 wt % and a biocompatible ceramic in an amount of 5 to 15 wt %;
        the cartilage regeneration layer is coupled to the bone regeneration layer with at least one biocompatible glue selected from the group consisting of fibrin glue, gelatin glue, polyurethane-containing glue, and cyanoacrylate-containing glue;
        the bone regeneration layer comprises pores in the size of 100 µm to 700 µm, and the cartilage regeneration layer comprises pores in the size of 50 µm to 700 µm;
        the biodegradable polymer is poly-caprolactone (PCL);
        the biocompatible ceramic is hydroxyapatite (HA);
        the cartilage regeneration layer is a cell-fixed biodegradable polymer support body consisting of alginate; and
        the bone regeneration layer and the cartilage regeneration layer are manufactured separately by a bioplotting technique of a rapid prototype method, and then securely coupled to each other.
2. The complex support body for regenerating bone-cartilage according to claim 1, wherein the cells that can be differentiated into cartilage cells is at least one cells selected from the group consisting of: mesenchymal stem cells and interstitial cells, which are isolated from any one of bone marrow, muscle, fat, umbilical cord, amnion and amniotic fluid; and precursor cells, which are derived from the cells and can be differentiated into cartilage cells.

* * * * *